US009672331B2

(12) United States Patent
McKinney et al.

(10) Patent No.: US 9,672,331 B2
(45) Date of Patent: *Jun. 6, 2017

(54) SYSTEMS AND METHODS FOR COMPUTER MODELS OF ANIMAL FEED

(71) Applicant: Alltech, Inc., Nicholasville, KY (US)

(72) Inventors: Kyle McKinney, Lexington, KY (US); Allyson Lovell, Lexington, KY (US); Benjamin Henry, Shelbyville, KY (US); Patrick Becker, Lexington, KY (US); Rebecca A. Timmons, Lexington, KY (US)

(73) Assignee: ALLTECH, INC., Nicholasville, KY (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/109,926

(22) Filed: Dec. 17, 2013

(65) Prior Publication Data

US 2015/0169847 A1 Jun. 18, 2015

(51) Int. Cl.
| | |
|---|---|
| *G01N 33/48* | (2006.01) |
| *G01N 33/50* | (2006.01) |
| *G06F 19/00* | (2011.01) |
| *G01N 21/359* | (2014.01) |
| *A23K 10/14* | (2016.01) |
| *A23K 50/75* | (2016.01) |
| *A23K 50/30* | (2016.01) |
| *G01N 21/68* | (2006.01) |

(52) U.S. Cl.
CPC .......... *G06F 19/704* (2013.01); *A23K 10/14* (2016.05); *A23K 50/30* (2016.05); *A23K 50/75* (2016.05); *G01N 21/359* (2013.01); *G06F 19/3437* (2013.01); *G01N 21/68* (2013.01); *G01N 2201/129* (2013.01)

(58) Field of Classification Search
None
See application file for complete search history.

(56) References Cited

U.S. PATENT DOCUMENTS

| | | | | |
|---|---|---|---|---|
| 3,437,489 | A | * | 4/1969 | Arakawa ................ A23K 10/22 426/541 |
| 5,922,343 | A | | 7/1999 | Stucker |
| 6,008,053 | A | | 12/1999 | Williams |
| 6,040,188 | A | * | 3/2000 | Holman ........................... 436/71 |
| 6,166,382 | A | | 12/2000 | Baker et al. |
| 6,532,420 | B1 | | 3/2003 | Haeffner et al. |
| 6,750,035 | B1 | | 6/2004 | Schasteen et al. |
| 7,174,672 | B2 | | 2/2007 | Beck |
| 7,490,437 | B1 | | 2/2009 | Beck |
| 8,067,238 | B2 | | 11/2011 | Sjoeholm et al. |
| 8,357,408 | B2 | | 1/2013 | Lassen et al. |
| 2003/0028328 | A1 | | 2/2003 | Julia et al. |
| 2005/0000457 | A1 | | 1/2005 | Beck |
| 2006/0036370 | A1 | * | 2/2006 | St-Pierre ........................... 702/19 |
| 2009/0047266 | A1 | * | 2/2009 | Svendsen et al. ........... 424/94.2 |
| 2009/0061055 | A1 | | 3/2009 | Newcomb et al. |
| 2009/0272889 | A1 | | 11/2009 | Combs et al. |
| 2012/0114770 | A1 | | 5/2012 | Regina et al. |
| 2012/0271449 | A1 | | 10/2012 | Weakley |

FOREIGN PATENT DOCUMENTS

| | | |
|---|---|---|
| WO | 8302158 A1 | 6/1983 |
| WO | 0115548 A1 | 3/2001 |
| WO | 2009059176 A2 | 5/2009 |

OTHER PUBLICATIONS

Balthrop et al., "Quality Assurance for Animal Feed Analysis Laboratories (Manual)", FOA Animal Production and Health Manual 14:1-178 (2011).
Boisen S., A multienzyme assay for pigs, A Model for Feed Evaluation Based on Invitro Digestible Dry Matter and Protein, Invitro Digestion for Pig and Poultry, 10:136-139 (1990).
Hansen, "The Use of Computer Modeling Techniques in Near Infrared Spectroscopy", Proceedings of 2008 IEEE International Symposium on IT in Medicine and Education, IEEE Press, Xiamen, China , p. 3 (Dec. 12-14, 2008).
International Search Report and Written Opinion mailed May 22, 2014, for International Patent Application PCT/US2014/015729.
International Search Report and Written Opinion mailed May 19, 2014, for International Patent Application PCT/US2014/015736.
International Search Report and Written Opinion mailed May 12, 2014, for related International Patent Application PCT/US2014/015740.
Kim, T.W., et al., "An Improved Method for a Rapid Determination of Phytase in Animal Feed"; J. Animal Science, 83:1062-1067 (2005).
Mentink et al., "Utility of Near-Infrared Reflectance Spectroscopy to Predict Nutrient Composition and In Vitro Digestibility of Total Mixed Rations", J. Dairy Sci. 89(6):2320-2326 (Jun. 2006).
Miller, "Use of Dintrosalicylic Acid Reagent for Determination of Reducing Sugar"; Anal. Chem 31:426-428 (1959).
Opitz et al., "Prediction of Digestibility and Energy Concentration of Catch Crops—A Comparison of Laboratory methods", 58(1-4):1-7, Article retrieved from the internet: https://diebodenkultur.boku.ac.at/volltexte/band-58/heft-1-4/opitz.pdf (2007).
Remington's Pharmaceutical Sciences, 18th Edition, Mack Publishing p. 1288-1300 (1990).

(Continued)

*Primary Examiner* — Russell S Negin
(74) *Attorney, Agent, or Firm* — Kilyk & Bowersox, P.L.L.C.; Valerie Calloway

(57) ABSTRACT

The present application provides systems and methods for analyzing animal feeds and for adjusting animal feeds to improve the digestibility of animal feed components. Digestibility of animal feed can be determined by performing in vitro digestion of the feed and analyzing concentrations of residual components in the digested feed by NIR spectroscopy. Animal feed compositions can be adjusted to improve digestibility of components in the feed. The systems and methods of the present application can be used to determine the effect of an additive on the digestibility of feed.

18 Claims, 5 Drawing Sheets

(56) References Cited

OTHER PUBLICATIONS

Smith et al., "The Use of Near-Infrared Reflectance Spectroscopy to Predict the Moisture, Nitrogen, Calcium, Total Phosphorus, Gross Energy, and Phytate Phosphorus Contents of Broiler Excreta", Poult Sci., 80(3):314-319 (Mar. 2001).

Boisen et al.,"Prediction of the apparent ileal digestability of protein and amino acids in feedstuffs and feed mixtures for pigs by in vitro analyses," Animal Feed Science and Technology, 1995, 51:29-43.

Coca-Sinova et al., "Apparent Ileal Digestibility of Energy, Nitrogen, and Amino Acids of Soybean Meals of Different origin in broilers," Poultry Science, 2008, 87:2613-2623.

Kempen, T., NIR technology: can we measure amino acid digestibility and energy values? 12th Annual Carolina Swine Nutrition Conference, Nov. 1996,1-12.

Kempen et al., "Near-Infrared Reflectance Spectroscopy in Precision Feed Formulation," J. Appl. Poultry Res., 1997, 6:471-477.

Undersander et al., "Forage Analyses Procedures," National Forage Testing Association, Jul. 1993, 1-139.

Spiehs, M., "Nutritional and Feed Strategies to Minimize Nutrient Losses in Livestock Manure," Regents of the University of Minnesota, 2005:1-5.

Boyce et al., "A Series of Enzymology-Based Experiments Designed to Mimic an Applied Research Project," Biochemistry and Molecular Biology Education, 2005, 33(6): 420-425.

Putnam et al., "Forage Quality and Testing," ANR Publication 8302, Feb. 2008, 1-25.

Tilley et al., "A Two-Stage Technique for the In Vitro Digestion of Forage Crops," J. Brit. Grassi. Soc., 1963, 18:104-111.

Ball et al., "Understanding forage quality," American Farm Bureau Federation Publication, 2001, 1-18.

Alfalfa, A Renewed Health, 2015, 1-4.

Gous et al., "Correlation between NIRS generated and chemically measured feed quality data in barley (Hordeum vulgare), and potential use in QTL analysis identification," Euphytica, 2012; 188:325-332.

Reese, D., "Utilization of grain by swine and poultry," passel.unl. edu., 2011; 1-9.

Shelton et al., "Adding phytase proves positive for poultry," swine diet, LSU, 2005; 1-3.

Ru et al., "Application of near infrared spectroscopy (NIR) for monitoring the quality of milk, cheese, meat and fish," Asian-Aus. J. Anim. Sci., 2000; 13(7):1017-1025.

Hervera, M. et al., "Use of near-infrared spectrascopy to predict energy content of commercial dog food," J. Anim. Sci., Oct. 2012, vol. 90, No. 12, pp. 4401-4407.

\* cited by examiner

SYSTEMS AND METHODS FOR COMPUTER MODELS OF ANIMAL FEED

FIELD

The present invention relates to systems and methods for adjusting animal feeds. In particular, the present application relates to in vitro systems and methods for analyzing animal feed for digestibility of nutrients.

BACKGROUND

Nutrients in animal feed are made available to the animal by digestion of the feed in the animal's gastrointestinal tract. Nutrients that are digested are absorbed and used by the animal for energy, growth, and development. Nutrients that are not digested, for the most part, pass through the intestinal tract of the animal decreasing the nutritional value of the feed. Digestibility of animal feed can be assessed by using in-vitro or in vivo digestion models and analyzing remaining nutrients in the digested feed by wet chemistry analytical methods. A drawback of the existing methods is that they are specific to a particular feed, expensive, and time consuming. It would, therefore, be beneficial to provide for a broadly applicable, less expensive and less time-consuming way to analyze the digestibility of animal feed.

SUMMARY

The present application relates to systems and methods for analyzing animal feeds and for adjusting animal feeds to improve the digestibility of animal feed components. In particular, the present application relates to in vitro digestion of a sample of animal feed and NIR analysis, as defined herein, of the sample of digested feed to determine digestibility of the animal feed components. In embodiments of the present application, a sample of an animal feed is digested using an in vitro procedure that has been designed to be similar to in vivo animal digestion. The sample of digested animal feed is scanned using NIR spectroscopy to generate spectral data that is compared to a computer model to provide a predicted concentration of at least one residual component in the sample of digested animal feed. The prediction of the concentration of at least one residual component allows a determination of the digestibility of that component in the animal feed composition. For example, protein is a component of animal feed compositions, and after digestion, residual amounts of protein are determined and provide a measure of the digestibility of the protein in the sample of animal feed. Animal feed compositions can be selected and/or adjusted to improve digestibility of components such as protein, phosphorus, carbohydrates, fats, gross energy, or fiber. Adjusting animal feed compositions comprises adding one or more post additives. Various post-additives can be tested to determine whether such post-additives improve the digestibility of animal feed components.

The present application includes a method of analyzing feed comprising digesting a sample of animal feed in vitro using at least one enzyme to generate digested animal feed comprising at least one residual component; scanning the digested animal feed using NIR spectroscopy to generate spectral data; and comparing the spectral data to a computer model of the residual component to generate a predicted concentration of the at least one residual component of the digested animal feed. Methods as described herein are methods of using NIR computer models to predict the type and quantity of residual components of in vitro digested animal feed sample. In embodiments, such methods are useful to select a feed composition and/or to adjust the feed composition to improve digestibility of feed components.

In embodiments of the present application, digesting a sample of animal feed comprises using pepsin or pancreatin or both. In other embodiments, digesting a sample of animal feed further comprises separating the digested sample into a solid component and a liquid component, and scanning the digested animal feed comprises scanning the solid component. In yet other embodiments, the at least one residual component is selected from the group consisting of protein, phosphorous, fat, gross energy, carbohydrates, and fiber. In other embodiments, the sample of animal feed comprises a pre additive. In embodiments, the pre additive comprises at least one enzyme.

In embodiments of the present application, the spectral data is compared using a computer implemented method comprising receiving spectral data from the digested sample and comparing the spectral data to a computer model of the residual component to obtain a predicted concentration of the at least one residual component.

In embodiments of the present application, the method of claim 1, further comprises: adjusting the animal feed composition to obtain a predetermined nutritional profile for the animal based on the predicted concentration of the at least one residual component of the sample of digested animal feed. In other embodiments, adjusting the animal feed composition to obtain a predetermined nutritional profile for the animal comprises adding at least one post additive. In embodiments, the post additive comprises an enzyme.

The present application further includes adjusting animal feed composition comprising steps of: identifying a predetermined nutritional profile of a feed component in the animal feed composition; predicting a concentration of a residual component of the feed component in an animal feed composition by a method comprising: digesting the sample of the animal feed in vitro using at least one enzyme to generate digested animal feed comprising at least one residual component; scanning the digested animal feed using NIR spectroscopy to generate spectral data; comparing the spectral data to a computer model of the at least one residual component to generate a predicted concentration of the residual component; and adjusting the animal feed composition to obtain the predetermined nutritional profile of the feed component based on the predicted concentration of the at least one residual component. In embodiments of the present application, the feed component is selected from the group consisting of protein, phosphorous, fat, gross energy, carbohydrates, fiber and combinations thereof. In other embodiments, the at least one residual component is selected from the group consisting of protein, phosphorous, fat, gross energy, carbohydrates, and fiber.

In embodiments of the present application, digesting a sample of animal feed comprises using pepsin or pancreatin or both. In other embodiments, digesting a sample of animal feed further comprises separating the digested sample into a solid component and a liquid component, and scanning the digested animal feed comprises scanning the solid component. In other embodiments, the sample of animal feed comprises a pre additive. In embodiments, the pre additive comprises at least one enzyme.

In embodiments of the present application, the spectral data is compared using a computer implemented method comprising receiving spectral data from the digested sample and comparing the spectral data to a computer model of the residual component to obtain a predicted concentration of the at least one residual component.

In embodiments of the present application, adjusting the animal feed composition comprises adding a post additive to the feed. In embodiments, the post additive comprises at least one enzyme. In embodiments, the post additive adjusts the amount of the residual component in the digested feed.

The present application also includes a method of developing a computer model for analyzing feed comprising steps of: digesting a plurality of samples of animal feed in vitro using at least one enzyme to generate a plurality of digested animal feed samples, wherein each of the plurality of digested animal feed samples comprises at least one residual component; scanning each of the plurality of digested animal feed samples using NIR spectroscopy to generate spectral data for each of the plurality of digested animal feed samples; determining the concentration of the at least one residual component in each of the plurality of digested animal feed samples using a wet chemistry method; and generating a computer model by establishing a predictive relationship between the concentration of the at least one residual component of each of the plurality of digested animal feed samples to the spectral data of a corresponding sample of the plurality of digested animal feed samples.

In some embodiments of the present application, the step of scanning each of the plurality of digested feed samples further comprises the step of mathematically manipulating the spectral data of each of the plurality of digested animal feed samples. In other embodiments, generating a computer model comprises a computer implemented method comprising steps of: receiving spectral data for each of the plurality of digested animal feed samples; relating the spectral data for each of the plurality of digested animal feed samples to the concentration of the at least one residual component in a corresponding sample of the plurality of digested animal feed samples; and establishing a predictive relationship based on the spectral data and the concentration of the at least one residual component of the plurality of digested animal feed samples to generate the computer model.

In embodiments of the present application, digesting the plurality of samples of animal feed comprises using pepsin or pancreatin or both. In other embodiments, digesting a sample of animal feed further comprises separating the digested sample into a solid component and a liquid component, and scanning the digested animal feed comprises scanning the solid component. In yet other embodiments, the at least one residual component is selected from the group consisting of protein, phosphorous, fat, gross energy, carbohydrates, and fiber.

In embodiments of the present application, the wet chemistry method comprises analyzing each sample of the plurality of digested feed samples for the concentration of the at least one residual component selected from the group consisting of protein, phosphorous, fat, gross energy, carbohydrates, and fiber. In other embodiments, the wet chemistry method comprises mixing the solid component with a liquid to form a mixture; and analyzing the composition of the mixture for the concentration of the at least one residual component selected from the group consisting of protein, phosphorous, fat, gross energy, carbohydrates, and fiber in each of the plurality of digested animal feed samples.

DETAILED DESCRIPTION

Definitions

Figure 1:
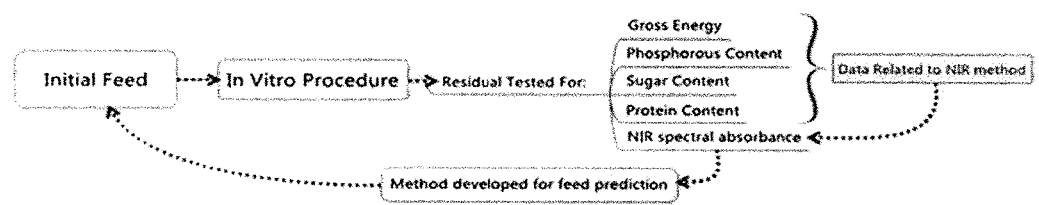
FIG. 1 shows a schematic of embodiments of methods of the present application.

The articles "a" and "an" are used herein to refer to one or to more than one (i.e. to at least one) of the grammatical object of the article. By way of example, "an element" means one element or more than one element.

As used in this application, the term "additive(s)" refers to a substance added to another substance. For example, an additive can be added to animal feed to improve digestibility of one or more feed components. An additive comprises an enzyme, a mixture of enzymes, a protein, a vitamin, a mineral, grains, maltodextrin, a supplement, and combinations thereof. A "pre-additive(s)" is a substance that is present as a component of an animal feed sample and is not added to the feed sample at the time of or just prior to analysis. A pre-additive is typically already present in the animal feed used in the field and includes, but is not limited to, an enzyme or mixture of enzymes. A "post-additive" is a substance that is added to the sample of animal feed composition at the time of or just prior to analysis. A post-additive is typically being added to the feed sample to determine if the post-additive alters the digestibility of a feed component and includes, but is not limited to, an enzyme or mixture of enzymes.

As used in this application, the term "analyte(s)" refers to a chemical constituent, the properties of which (e.g., concentration) are to be determined using an analytical procedure.

As used in this application, the term "animal(s)" refers to non-human animals raised or used as a source of food. For example, animals include, but are not limited to, domesticated livestock such as cattle, goats, sheep, horses, poultry, buffalo, alpaca, llamas, donkeys, mules, rabbits, chickens, geese, turkeys, or pigs.

As used in this application, the term "computer model(s)" refers to a model that is predictive of the concentration of a component of a mixture (e.g., feed) based on spectral data obtained, for example, by NIR. In embodiments of the present application, the spectral data from each sample of a plurality of samples is related to a concentration of a residual component as determined by analytical wet chemistry chemical methods for each sample. The model can be used to provide an estimation of the amount (e.g., concentration)

of a constituent of an unknown sample by comparing the spectrum of the unknown sample to the model.

As used in this application, the terms "digesting", "digested", and "digestion" refer to changing a material by breaking down or decomposing its components. In some embodiments, digesting is an in vitro process using, for example, heat, chemicals, and/or enzymes to break down the components of the material.

As used in this application, the term "feed(s)" or "animal feed(s)" refers to material(s) that are consumed by animals and contribute energy and/or nutrients to an animal's diet. Animal feeds typically include a number of different components that may be present in forms such as concentrate(s), premix(es) co-product(s), or pellets. Examples of feeds and feed components include, but are not limited to, Total Mixed Ration (TMR), corn, soybean, forage(s), grain(s), distiller grain(s), sprouted grains, legumes, vitamins, amino acids, minerals, molasses, fiber(s), fodder(s), grass(es), hay, straw, silage, kernel(s), leaves, meal, soluble(s), and supplement(s). Some components or constituents of components of the animal feed are detectable by Near Infrared Spectroscopy (NIR). Other components of animal feed are not detectable or may be poorly detectable by NIR because of low concentration, presence in a complex that masks the component, or because the physical or chemical characteristics of the component do not lend themselves to NIR detection.

As used in this application, the term "in vivo" refers to processes occurring within a living biological organism.

As used in this application, the term "in vitro" refers to processes occurring in an artificial environment outside the living organism and to biological processes or reactions that would normally occur within an organism but are made to occur in an artificial environment. In vitro environments can include, but are not limited to, test tubes and cell culture.

As used in this application, the term "nutrient(s)" refers to a substance that is needed for an organism to live and/or grow. Nutrients include, but are not limited to, compounds such as protein, fat, carbohydrates (e.g., sugars), fiber, vitamins, calcium, iron, niacin, nitrogen, oxygen, carbon, phosphorus, potassium, sodium chloride, and mixtures thereof.

As used in this application, the term "NIR spectroscopy" or "NIR" refers to the scanning and measuring the absorbance of samples using near infra-red radiation with wavelengths in the range of 800-2500 nm to create an absorbance spectrum. NIR is used to measure absorbance by chemical bonds caused by overtone and combination vibrations and is most useful as an indirect quantitative method of analysis. NIR spectroscopy is used to predict the amount or type of a chemical constituent of a substance by comparing the spectrum obtained by scanning the sample to a calibration (e.g., a computer model). The spectra can be further manipulated mathematically, e.g., by Fourier transformation. NIR spectrometers can be configured to operate either in a reflectance or transmittance mode. Specific examples of NIR equipment include Bruker MPA FT-NIR (available from Bruker Optics, Inc., Billerica, Mass.), and Antaris™ FT-NIR Analyzer (available from Thermo Scientific in Waltham, Mass.).

As used in this application, a "predetermined nutrition profile(s)" refers to a desired amount of a feed component or components in an animal feed for which digestibility is a relevant characteristic. A nutritionist or a farmer can set a desired amount of a component in a particular feed. For example, the amount of protein or additive in the animal feed may need to be adjusted to take into account the digestibility of the protein in the animal feed as determined using the methods described herein. An animal feed with protein that is in a form that is less digestible may require an increase in protein in the animal feed and/or the addition of a post additive that increases the digestibility of protein in that animal feed to achieve the desired amount.

As used in this application, a "predicted concentration(s)" refers to an amount of a nutrient or residual component detected in a digested feed sample using NIR spectroscopy and a computer model. In embodiments of the present application, the digested animal feed is scanned using NIR spectroscopy to generate spectral data; and the spectral data is compared to a computer model of the at least one residual component to generate a predicted concentration of the at least one residual component of the digested animal feed. The predicted concentration is an estimate of the actual concentration of the at least one residual component in the sample.

As used in this application, the term "residual component(s)" refers to a component that remains in a mixture after one or more components have been removed from and/or changed in the mixture. In embodiments of the present application, a residual component is an individual component that includes, but is not limited to, protein, phosphorous, fat, carbohydrates, and fiber. In other embodiments, a residual component is a characteristic of the digested sample including but not limited to moisture content, gross energy, and ash content.

As used in this application, the term "sample(s) of animal feed" refers to a representative portion of an animal feed. In embodiments of the present application, a representative portion of an animal feed contains the same components in similar proportions to that of the animal feed. A representative sample is preferably homogenous or substantially homogenous.

As used in this application, the term "spectral data" refers to the data obtained when radiation interacts with a material. For example, spectral data is obtained when radiation at near infrared wavelengths interacts with a material and is absorbed by vibrations of chemical bonds in the material. The intensity of the absorbance can be measured by measuring the amount of radiation reflected back from or transmitted through the material at a given wavelength. The intensity of absorption at a given wavelength responds to the amount and types of chemical bonds in the material.

Detailed Description

The present application relates to systems and methods for analyzing animal feeds. In particular, the present application relates to systems and methods for analyzing the digestibility of feed components in animal feed. Additionally, the systems and methods of the present application are used to determine the effect of a pre-additive and/or a post-additive on the digestibility of a feed component.

Methods of analyzing animal feed for feed components involve procedures (e.g., digestion methods and wet chemistry methods) that are costly and time consuming, often requiring multiple pieces of laboratory equipment and multiple assays for different components. A single analysis using wet chemical methods involves splitting a sample into different portions for analysis of residual components such as protein, sugars, phosphorus, gross energy, and fats. This analysis destroys the sample.

In contrast, the systems and methods provided in the present application provide the predicted concentration of multiple components using a single sample, are rapid, decrease the time and cost for analysis, and allow for adjusting feed composition to improve the digestibility of feed components in the animal feed composition.

Systems and Methods for Developing a Computer Model

The present application includes a method of developing a computer model for analyzing feed comprising steps of: digesting a plurality of samples of animal feed in vitro using at least one enzyme to generate a plurality of digested animal feed samples, wherein each of the plurality of digested animal feed samples comprises at least one residual component; scanning each of the plurality of digested animal feed samples using NIR spectroscopy to generate spectral data for each of the plurality of digested animal feed samples; determining the concentration of the at least one residual component in each of the plurality of digested animal feed samples using a wet chemistry method; and generating a computer model by establishing a predictive relationship between the concentration of the at least one residual component of each of the plurality of digested animal feed samples to the spectral data of a corresponding sample of the plurality of digested animal feed samples.

In Vitro Digestion Assay

To develop the computer model, a plurality of digested feed samples are generated and analyzed. Animal feed samples are digested in vitro using at least one enzyme.

The components of animal feed samples vary depending on the source of the feed sample. For example, farms located in different geographic regions and/or having different breeds of an animal may have a feed with different components. In addition, a nutritionist or a farmer can set a desired amount of a component in a particular feed or select a particular feed based on the desired amount of the component. Examples of feeds and feed components include, but are not limited to, Total Mixed Ration (TMR), corn, soybean, forage(s), grain(s), distiller grain(s), sprouted grains, legumes, vitamins, amino acids, minerals, molasses, fiber(s), fodder(s), grass(es), hay, straw, silage, kernel(s), leaves, meal, soluble(s), and supplement(s).

In embodiments of the present application, a plurality of different animal feed samples for a particular animal such as poultry or swine are digested. The plurality of samples has a sufficient number of samples to provide a computer model with a coefficient of determination ($R^2$) value of at least 50, 60, 70, 80, 90, or 100, or any number between 50 and 100. In embodiments of the present application, a plurality of samples includes at least 25, 35, 50, or a 100 or more samples. In specific embodiments, a plurality of samples includes at least 50 unique samples.

In embodiments of the present application, each sample is digested in vitro with at least one enzyme. In embodiments of the present application, the enzyme and conditions of digestion are selected to be similar to in vivo digestion of the type of animal. In embodiments, the animal is a monogastric animal. In embodiments, the animal is a swine or a poultry. For example, one enzyme that is involved in digestion of the stomach is pepsin, and an enzyme involved in intestinal digestion is pancreatin. One or both of these enzymes are employed in the in vitro digestion assay.

In embodiments of the present application, pepsin is used at an acidic pH of less than 7, 6, 5, 4, 3, 2 or any number in between. In some embodiments, the digestion with pepsin is conducted for a time that corresponds to in vivo digestion in the stomach of the animal, for example, at least 1 to 6 hours for a swine. For example, about 30 minutes to 2 hours for poultry. Conditions of pH, temperature, and time may be adjusted depending on the type of animal.

In embodiments of the present application, a sample is digested with pancreatin. When a sample is digested with pancreatin, the digestion is conducted at a pH of at least 6.0. In some embodiments, the digestion with pancreatin is conducted for a time that corresponds to in vivo digestion in the intestine of the animal, for example, at least 18 hours to 48 hours for a swine. For example, about 30 minutes to 2 hours for poultry. Conditions of pH, temperature, and time may be adjusted depending on the type of animal.

In some embodiments, the sample of animal feed is digested with pepsin followed by digestion with pancreatin under conditions that are similar to in vivo digestion of the sample in the animal species. Animals include animals raised or used a source of food including but not limited to cattle, goats, sheep, horses, poultry, buffalo, alpaca, llamas, donkeys, mules, rabbits, chickens, geese, turkeys, or pigs.

In some embodiments of the present application, more or less steps may be present in the in vitro digestion assay depending on the in vivo digestion process of the animal. For example, for swine, an in vitro digestion assay includes, but is not limited to, a stomach phase, and an intestine phase. For example, for poultry an in vitro digestion assay includes, but is not limited to, a crop phase, a gizzard phase, and a small intestine phase. In stomach or gizzard phases, the digestion is conducted at an acidic pH and includes an enzyme like pepsin. In the intestine phase digestion is conducted at a neutral to slightly acidic pH and includes an enzyme like pancreatin. Other digestive enzymes may be utilized. One or more digestive enzymes are employed in any one or any combination of phases.

Digested animal feed samples comprise at least one residual component. A residual component is a component may remain after digestion of a feed component in the feed sample. For example, a feed component in a feed sample is protein but not all protein may be digested in vivo or in the in vitro assay so that a residual protein component remains after digestion. Other residual components include phosphorous, fat, gross energy, carbohydrates, or fiber.

In embodiments of the present application, a method of digesting a plurality of samples comprises separating each sample into a liquid component and a solid component. Typically such separation occurs using centrifugation, or filtration.

Each of the plurality of digested samples is analyzed by NIR spectroscopy and wet chemical methods.

NIR Spectroscopy

Each of the plurality of the digested samples of animal feed is scanned using NIR spectroscopy to generate spectral data. Near Infrared Spectroscopy (NIR, also known as NIRS) is a spectroscopic technology that is used for producing a predicted concentration of at least one residual component of the sample (e.g., the concentration of an analyte). NIR relies on wavelengths in the range of 800-2500 nm, and is most useful for measuring overtone and combination vibrations in molecules. Because NIR measurements typically require little or no sample preparation, most samples can be measured without pretreatment, manipulation, or destruction.

A typical NIR instrument usually scans the sample multiple times across a selected wavelength range and averages the scans to produce a spectrum. NIR instruments can be configured to measure either transmittance of transparent samples or reflectance for opaque samples. Because of considerable overlap in overtone and combination bands of molecules, NIR technologies typically rely on multivariate calibration techniques. NIR computer models can comprise models (e.g., calibrations) for multiple analytes and can include tens, hundreds, or even thousands of samples.

In embodiments of the present application, the spectral data is processed to place it in a form useful to generate a model. In embodiments of the present application, the spectral data is mathematically manipulated to minimize noise, extract principal components, and/or to subtract background.

In embodiments of the present application, the digested samples are separated into a liquid and a solid component and the solid component is scanned. The solid component comprises at least one residual component. NIR scans can identify more than one component of a mixture as well as provide a predicted concentration of each of the components in a mixture. The NIR scans generate spectral data that is used to develop a computer model for each of the residual components.

Chemical Analysis

The samples that are scanned on the NIR are also analyzed using primary analytical methods, i.e., wet chemistry methods. Wet chemistry methods include primary reference methods used for the analysis of components such as protein, phosphorous, fat, gross energy, carbohydrates, or fiber. Such assays are known to those to skill in the art. For protein, methods of analysis include determination of nitrogen and analysis by ultraviolet visible spectroscopy. For phosphorus, methods of analysis include determination of phosphorus by inductively coupled plasma system. Gross energy can be determined in a bomb calorimeter.

Analytical chemical methods can be used on liquid or dry samples. In embodiments of the present application, a digested sample is separated into a liquid component and a solid component. Both components can be analyzed using wet chemistry methods. For example, released phosphorus can be determined in the liquid component and residual phosphorus can be determined in the solid component. In some embodiments, the solid component is mixed with a liquid in order to facilitate wet chemical analysis of at least one residual component in the solid component.

The wet chemical analysis provides a concentration of at least one residual component in each of the digested samples. In embodiments of the present application, multiple residual components are measured.

Generating a Computer Model

In embodiments of the present application, a method comprises generating a computer model by establishing a predictive relationship between the concentration of the at least one residual component of each of the plurality of digested animal feed samples to the spectral data of a corresponding sample of each of the plurality of digested animal feed samples.

The spectra of various samples are related to wet chemistry results using mathematical manipulation of data via a computer implemented method to produce the calibration. In embodiments of the present application, a computer implemented method comprises steps of: receiving spectral data for each of the plurality of digested animal feed samples; relating the spectral data for each of the plurality of digested animal feed samples to the concentration of the at least one residual component in a corresponding sample of each of the plurality of digested animal feed samples; and establishing a predictive relationship based on the spectral data and the concentration of the at least one residual component in each of the plurality of digested animal feed samples to generate the computer model.

Spectral data is generated upon scanning the digested samples. Spectral data may be mathematically processed to place it in a form useful to generate a model. In embodiments of the present application, the spectral data is mathematically manipulated to minimize noise, extract principal components, and/or to subtract background.

Spectral data from each sample is then related to the concentration of at least one residual component of the corresponding sample as determined by the wet chemical methods. Relating of the spectral data to the concentration of at least one residual component occurs when the concentration of the at least one residual component for the particular sample are input into the NIR spectrometer.

The relationship between the concentration of at least one residual component in each of the plurality of samples is used to generate a model using one or more statistical methods to establish a predicted relationship between the concentration of the at least one residual component in a sample and the spectral data for that data. Statistical methods include principal component analysis, linear regression analysis, or partial least squares analysis. Any number of statistical methods can be used to build a computer model for that residual component.

In embodiments of the present application, NIR models are characterized by coefficient of determination, $R^2$ value, that reflects the predictive power of the computer model. In embodiments of the present application, the $R^2$ values of the computer model are at least 50, 60, 70, 80, 90, or 100, or any number between 50 and 100.

A computer model is typically validated using a validation method. In embodiments of the present application, a validation method is a computer implemented method where the plurality of samples is divided into a model building set and a validation set. Assignment of the samples to a set is typically done randomly. The data from the model building set are utilized to build a model as described herein. The data from the validation set are used to test the predictive power of the model. The samples of the validation set are tested against the model to generate a predicted concentration of the at least one residual component. This predicted concentration is then compared to the actual concentration of the sample as determined by wet chemistry. This comparison allows a determination of $R^2$ value and/or standard error. Other types of validation such as a leave one out validation method can also be employed.

Once the computer model is generated it is stored within the NIR spectrometer. In embodiments of the present application, NIR spectrometer includes a microprocessor and memory having instructions to implement the computer implemented of generating a computer model or validating a computer model as described herein. In embodiments of the present application, the memory serves to store computer models for each residual component, and/or a database of spectral data for each sample. The computer model is useful to provide for a predicted concentration the at least one residual component of a sample with an unknown concentration of the at least one residual component.

According to embodiments of the present application, the systems of the present application include systems and equipment suitable for performing in vitro digestion of feed samples and NIR analysis of digested samples. According to other embodiments, the systems of the present application also include systems and equipment suitable for performing wet chemistry analysis of digested samples. According to exemplary embodiments, the system may comprise typical laboratory equipment and glassware, such as flasks, beakers, test tubes, scales, pipettes, incubators, shakers, stirrers, water baths, etc. The system may also comprise analyzers, such as an ICP, a nitrogen analyzer, and a bomb calorimeter.

According to embodiments, the system further comprises a NIR analyzer equipped with a computer and software suitable for operating the NIR and for developing and using a computer model (e.g., calibration). According to an alternative embodiment, the computer model may be stored on a remote computer, accessed by the computer via communications infrastructure, such as the internet. In an exemplary embodiment, the NIR is configured with a rotating sample cup assembly for scanning feed samples.

The methods and systems of the present application can be implemented as a combination of hardware and software. The software can be implemented as an application program tangibly embodied on a program storage device, or different portions of the software implemented in the user's computing environment (e.g., an applet) and on a reviewer's computing environment, where the reviewer may be located at a remote site (e.g., at a service provider's facility).

In the embodiments, the computer includes a processor unit. The processor unit operates to receive information, which generally includes spectral data (e.g., NIR spectra), and a database of known data (e.g., experimentally determined information (e.g., wet chemistry results) from a plurality of samples). This information received can be stored at least temporarily in a database, and data analyzed.

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

Systems and Methods for Analyzing Feed Samples

The present application includes methods of using a computer model of at least one residual component of an animal feed. Such methods are useful to compare different feed compositions and to adjust feed compositions to improve digestibility of feed components. In embodiments of the present application, a method of analyzing feed comprises steps of: digesting a sample of animal feed in vitro using at least one enzyme to generate digested animal feed comprising at least one residual component; scanning the digested animal feed using NIR spectroscopy to generate spectral data; and comparing the spectral data to a computer model of the at least one residual component to generate an predicted concentration of the at least one residual component of the digested animal feed.

As described previously, the samples of animal feeds can differ in components and can be obtained from different sources. In embodiments of the present application, a sample of animal feed comprises a pre-additive. A pre-additive includes an enzyme. Feed samples are digested using in vitro digestion with at least one enzyme as described herein. Samples used in this method have an unknown amount of at least one residual component after digestion.

The samples are being analyzed, for example, to identify the concentration of the at least one residual component in the digested sample. Residual components include, but are not limited to, protein, phosphorous, fat, gross energy, carbohydrates, and fiber. Analysis of residual components is useful to determine the digestibility of the feed sample. Digested samples are scanned using NIR spectroscopy and the spectra are stored in the NIR spectrometer. Feed samples of different types can be compared to one another in order to identify which feed composition provides for greater digestibility of the feed component. For example, if a first feed composition has a lower residual protein, gross energy or phosphorus component after digestion than another feed composition, then the first feed composition is selected.

When the computer model is used to analyze samples, the spectrum produced by scanning the sample is compared to the model that then returns a predicted concentration of the composition of the sample. A NIR measurement typically lasts only a few minutes and returns results immediately, making NIR measurements fast and convenient.

According to embodiments of the present application, NIR measurements are combined with an in vitro digestion assay to determine the digestibility of a sample. Existing NIR methods include scanning feed samples as-is (i.e., without sample pre-treatment) and estimating the amount of a component of a feed sample. However, such methods only work to predict the initial composition of the feed and are not able to differentiate which feed samples will have improved digestibility. Therefore, a method has been developed where feed samples are processed using a digestion assay and the digested sample is scanned using NIR, allowing for a more accurate prediction of the digestibility of the components of the feed sample, while saving time and resources because the digested sample does not need to be analyzed using wet chemistry methods. The method combines the information conveyed by the digestion assay and the speed and convenience of NIR measurement.

In embodiments of the present application, the present application includes digesting a first sample of an first animal feed composition and digesting a second sample of a second animal feed composition with at least one enzyme, wherein the first and second feed composition differ from one another in at least one feed component; scanning the first and second sample of the digested animal feed using NIR spectroscopy to generate spectral data for at least one residual component of each sample; comparing the spectral data from each sample to a computer model of the at least one residual component to generate a predicted concentration of the at least one residual component of the first and second sample of digested animal feed; and selecting the animal feed composition that has the desired or predetermined concentration of the at least one residual component by comparing the predicted concentration of the at least one residual component of the first and second sample of digested animal feed. In some embodiments, an animal feed composition is selected that provides for a decrease in a residual component such as protein, phosphorus or gross energy.

In embodiments of the present application, a method provides for determining the effect of a post-additive on digestibility of the feed sample. Such methods are useful to determine whether adding a post additive to a feed composition improves the digestibility of the feed or provides a feed composition that has a predetermined nutritional profile of a feed component. In embodiments of the present application, one or more post-additives are added to the feed sample prior to or at the time of digestion. Different additives can be compared for the ability to improve digestibility of a feed component. In embodiments of the present application a post-additive comprises at least one enzyme, a mixture of enzymes, or a substrate with a microbial source of enzymes.

In the present application, methods are also useful to compare the efficiency of feed compositions with different components. In that case, a first feed sample has a first composition, a second feed composition has a second composition, wherein the first and second feed compositions differ from one another in at least one feed component. In embodiments, the first and second feed compositions differ from one another by having a different component or the same component but in different amounts. In embodiments, the components that differ in presence or amount are selected from the group consisting of phosphorous, fat, protein, gross energy, carbohydrates, fiber, a pre-additive, and combinations thereof.

In embodiments of the present application, the present application includes digesting a first sample of an first animal feed composition and digesting a second sample of a second animal feed composition with at least one enzyme, wherein the second feed composition differs from the first composition by the presence of at least one post-additive or by having a different post-additive; scanning the first and second sample of the digested animal feed using NIR spectroscopy to generate spectral data for at least one residual component of each digested sample; comparing the spectral data from each sample to a computer model of the at least one residual component to generate a predicted concentration of the at least one residual component of the first and second sample of digested animal feed; and selecting the animal feed composition that has the desired or predetermined concentration of the at least one residual component by comparing the predicted concentration of the at least one residual component of the first and second sample of digested animal feed. In some embodiments, a post-additive is selected that provides for a decrease in a residual component such as protein, phosphorus or gross energy.

Systems and Methods for Adjusting Animal Feed

The present application includes methods of using a computer model of at least one residual component of an animal feed. Such methods are useful to compare different feed compositions and to adjust feed compositions to improve digestibility of feed components. In embodiments of the present application, adjusting animal feed composition comprises steps of: identifying a predetermined nutritional profile of a feed component of the animal feed composition; predicting a concentration of a residual component of the feed component in an animal feed by a method comprising: digesting a sample of the animal feed in vitro using at least one enzyme to generate digested animal feed comprising at least one residual component; scanning the digested animal feed using NIR spectroscopy to generate spectral data; comparing the spectral data to a computer model of the at least one residual component to generate a predicted concentration of the residual component; and adjusting the animal feed composition to obtain the predetermined nutritional profile of the feed component based on the predicted concentration of the at least one residual component.

Accordingly, in some embodiments, the present invention provides an efficient way to analyze feed (e.g., animal feed) for enzymatic effects on protein, fat, gross energy, digestible energy, phosphorous release, sugar release, fiber, carbohydrates, etc., and to determine the effect a post-additive has on the digestibility of the feed. The systems and methods described in the present application can be used to analyze a multitude of feeds for multiple components and can be updated rapidly without undergoing in vivo trials.

The present application finds use in the analysis of any number of animal feeds and is not limited to analysis of a particular feed. Animal feed is any foodstuff that is used specifically to feed domesticated livestock (e.g., cattle, goats, sheep, horses, poultry, buffalo, alpaca, llamas, donkeys, mules, rabbits, and pigs). Animal feeds often include Total Mixed Ration (TMR), corn, soybean, forage(s), grain(s), distiller grain(s), sprouted grains, legumes, vitamins, amino acids, minerals, molasses, fiber(s), fodder(s), grass(es), hay, straw, silage, kernel(s), leaves, meal, soluble(s), and supplement(s).

The digestibility of a feed component can be improved by adding one or more post-additives such as enzymes (e.g., digestive enzymes) to the feed. For example, enzymes such as phytase, protease, fungal protease, cellulase, xylanase, acid phosphatase, beta-glucanase, pectinase, and alpha amylase, can be added to the feed (i.e., used as additives) to improve digestibility. The enzymes may be provided in purified form, partially purified form, or crude form. The enzymes may be of natural (e.g., fungal) or synthetic origin, or may be produced in vitro (e.g., recombinant). In some embodiments, a protease (e.g., pepsin) is added. In some embodiments, commercially available enzyme or enzyme mixtures are added (e.g., Allzyme SSF, available from Alltech, Nicholasville, Ky.).

In order to determine whether adding a post-additive to a particular feed composition would be desirable, it is beneficial to know the digestibility components of the feed composition. According to an embodiment, the feed composition can be analyzed by digesting a sample of the animal feed in vitro to generate digested feed comprising at least one residual component, scanning the digested feed using NIR to generate spectral data, comparing the spectral data to a computer model of at least one residual component, and generating a predicted of the concentration of the residual component. The predicted of the concentration of the one or more residual components can be compared to a predeteimined or desired nutritional profile of the feed component. In some embodiments of the present application, if the amount of the residual component is higher than in the predetermined or desired nutritional profile of the feed component, the nutritional profile can be enhanced by adding one or more post-additives, such as enzymes (e.g., digestive enzymes).

A "predetermined nutrition profile(s)" refers to a desired amount of a feed component or components in an animal feed for which digestibility is a relevant characteristic. A nutritionist or a farmer can set a desired amount of a component in a particular feed. For example, the amount of protein or additive in the animal feed may need to be adjusted to take into account the digestibility of the protein in the animal feed as determined using the methods described herein. An animal feed with protein that is in a form that is less digestible may require an increase in protein in the animal feed and/or the addition of a post additive that increases the digestibility of protein in that animal feed to achieve the desired amount.

According to another embodiment, the system and method can be used to compare the digestibility or two or more feeds, one or more of which may comprise a post-additive, such as an enzyme (e.g., digestive enzyme). For example, the system and method can be used to show that one feed sample has a superior nutritional profile as compared to another feed sample because the one feed sample has a component that is more digestible.

The following examples are provided in order to demonstrate and further illustrate certain preferred embodiments and aspects of the present invention and are not to be construed as limiting the scope thereof.

EXAMPLES

Example 1

NIR Models

NIR models were created for digested samples of swine and poultry feed. The models can be used in conjunction with a digestion assay to evaluate the digestibility of feed samples by estimating the content of residual components in the digested samples.

FIG. 1 shows an exemplary scheme for methods of digesting and analyzing a feed sample as described herein. The figure shows that an initial feed sample was subjected to in vitro digestion and the digest was analyzed for residual amounts of gross energy, protein, phosphorus, and sugar content using NIR and wet chemistry.

Samples of poultry and swine feed were digested using a digestion assay that is similar to digestion of nutrients in vitro. The assay was modified from Boisen S., A multienzyme assay for pigs, Chapter 10, A Model for Feed Evaluation Based on Invitro Digestible Dry Matter and Protein, Invitro Digestion for Pig and Poultry, 1990, M. F. Fuller.

The digested samples were analyzed using wet chemistry methods for protein, gross energy and phosphorus. A final mass consisting of digested feed and liquid was separated into a solid component and a liquid component. The solid component was dried and the dried solids scanned using a NIR spectrometer. NIR models were created for protein, phosphorus, and gross energy in digested poultry feed, and for protein and gross energy in digested swine feed.

Digestion Assay

Samples of swine and poultry feed were digested using the following digestion assay. Some samples were altered by adding a post-additive (Allzyme SSF) during the assay.

Starting Materials:

Poultry and swine feed samples of various origins were used. Both poultry and swine feed samples were mainly composed of corn and soybean meal.

Allzyme SSF feed additive, available from Alltech, Nicholasville, Ky. was used as a source of added enzymes (e.g post additive) to the feed. Allzyme SSF contains an enzyme complex including at least 300 U phytase.

Reagents:
A. HCl: 0.2 M, 1M, 2 M, and 4 M
B. 0.6 M NaOH
C. 1M NaHCO$_3$
D. Pepsin from Sigma (P7012); 10 mg pepsin/mL de-ionized water or 2.25 mg pepsin/mL de-ionized water
E. Pancreatin from Sigma (P3292); 50 mg pancreatin/mL de-ionized water or 2.315 mg pancreatin/mL de-ionized water
F. 15% trichloroacetic acid (TCA)
G. Acetate buffer: 0.1 M (pH 6.0) and 0.2 M (pH 6.8)
H. Chloramphenicol solution; 5 mg chloramphenicol/1 mL alcohol
I. TCA stop solution
J. Color Reagent prepared from 3 volumes of 1 M Sulfuric Acid, 1 volume of 2.5% (w/v) Ammonium Molybdate, and 1 volume of 10% (w/v) Ascorbic Acid
K. DNS solution (stored in a dark bottle), prepared from dinitrosalisylic acid, NaOH, potassium sodium tartrate tetrahydrate and de-ionized water
L. Dextrose standards: 0 mg/mL; 0.2 mg/mL; 0.4 mg/mL; 0.6 mg/mL; 0.8 mg/mL; and 1.0 mg/mL
Phosphate standards: 0 µM; 5.625 µM; 11.25 µM; 22.5 µM; 45 µM; and 90 µM potassium phosphate in water.

Procedure

Enzyme Additive

To produce a liquid enzyme product to be used in the experiment as a post-additive, enzymes were extracted from Allzyme SSF with de-ionized water and diluted 1:2,500,000 with 0.1 M sodium acetate buffer.

Swine Digestion Assay

Primary Digestion—Stomach

Two grams of a ground swine feed sample were mixed with 49 mL of 0.1 M sodium acetate buffer. Some samples were altered by adding a post-additive by mixing with 1 mL of the liquid post additive prepared from the Allzyme SFF product described above. The pH of the solution was adjusted to 2 with HCl. 2.0 mL of pepsin solution (10 mg pepsin/mL de-ionized water) and 1.0 mL chloramphenicol solutions were added. The solution was stirred and placed in a 39° C. agitating water bath at 55 RPM for 6 hrs. The solution was stirred hourly.

Secondary Digestion—Small Intestine

After primary digestion, the samples were mixed with 20 mL of 0.2 M sodium acetate buffer and 10 mL of 0.6 M NaOH. The pH of the solution was adjusted to 6.8 with 0.6 M NaOH. 2.0 mL of pancreatin solution (50 mg pancreatin/mL de-ionized water) was added. The solution was stirred and placed in a 39° C. agitating (55 RPM) water bath for 18 hours. The solution was stirred and centrifuged at 14000 g for 20 min.

Poultry Digestion Assay

Crop Phase

Two and a half grams of a ground poultry feed sample were mixed with 6 ml of distilled water. Some samples were altered by adding a post-additive by mixing with 1 mL of the liquid post additive prepared from the Allzyme SFF product described above with 7 ml. of distilled water. The samples were incubated at 40° C. for 30 minutes.

Gizzard Phase

After incubation in the crop phase samples were adjusted to pH 3.0 with 1M HCl. 2.0 mL of pepsin solution (2.25 mg pepsin/mL de-ionized water) and 1.0 mL chloramphenicol solutions were added to each sample. The solution was stirred and placed in a 40° C. water bath for 45 minutes.

Small Intestine

After the gizzard phase, the samples were mixed with 1 mL of NaHCO$_3$ to obtain a pH of 6.5. 2.0 mL of pancreatin solution (2.315 mg pancreatin/mL de-ionized water) was added. The solution was stirred and placed in a 40° C. water bath for 60 minutes. The solution was stirred and centrifuged at 14000 g for 20 min.

Wet Chemistry Analysis

The in vitro digestion procedure left a final mass consisting of a solid portion of digested feed and a liquid portion. The sample was separated for further analysis into a solid component and a liquid component (i.e., supernatant). The solid component was freeze dried to give a final dry matter portion.

Equipment:
Varian 720-ES ICP for phosphorus analysis
Leco TruSpec CHN for nitrogen (protein) analysis
Parr 6100 bomb calorimeter for gross energy analysis Protein, Phosphorus and Gross Energy The final dry matter portion of the digested sample was analyzed for protein, phosphorus and gross energy. Protein content was determined using a nitrogen combustion analyzer and by converting the nitrogen content to protein. Phosphorus content was determined using an ICP (inductively coupled plasma) system. Gross energy content was determined using a bomb calorimeter.

NIR Model

Figure 2:
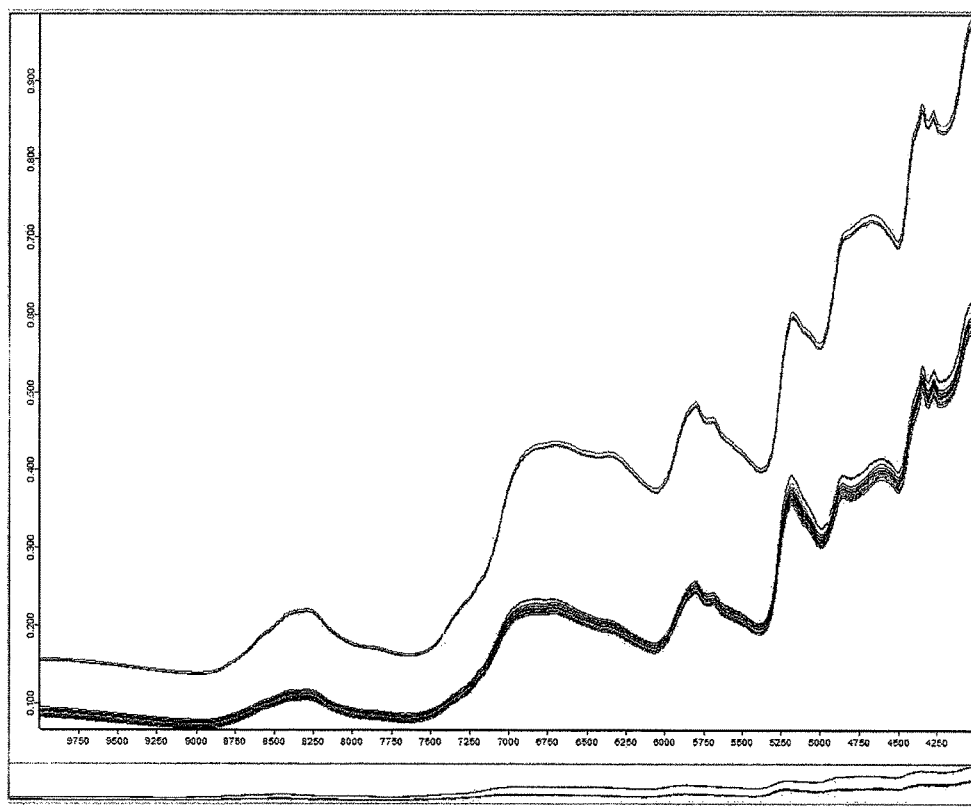
FIG. 2 shows an exemplary NIR spectral data of poultry feed samples processed according to an embodiment of the present application.

The final dry matter portion of the digested sample was scanned using a NIR rotating cup assembly to collect NIR reflectance data. The NIR scans of various samples were recorded and were correlated with the wet chemistry results for each sample to create a computer model for each component (protein, phosphorus and gross energy) of the digested samples.
Equipment:
Bruker MPA FT-NIR, model number 122000 with rotating cup assembly, available from Bruker Optics, Inc., Billerica, Mass.
Settings:
Resolution 16 cm$^{-1}$
Scans 32: the instrument was set to scan each sample 32 to times and to average the scans into a single scan file for each sample
Wavenumber range 10000 cm$^{-1}$–4000 cm$^{-1}$
Absorbance was measured using the "sphere macrosample" compartment
Results—Poultry Feed Digestion Assay Poultry feed samples were digested according to the digestion assay. Final dry matter portions of the digested samples were scanned on the NIR. An exemplary NIR scan of the digested poultry feed samples are shown in FIG. 2.

The digested samples were analyzed by wet chemistry methods for protein, phosphorus and gross energy. The protein content of the digested samples was in the range of 13-34%; the phosphorus content was in the range of 750-5900 ppm; and gross energy in the range of 3300-5200 cal/g. The protein, phosphorus and gross energy content of each sample were then correlated with the NIR scans to develop NIR models for each component.

Figure 3:
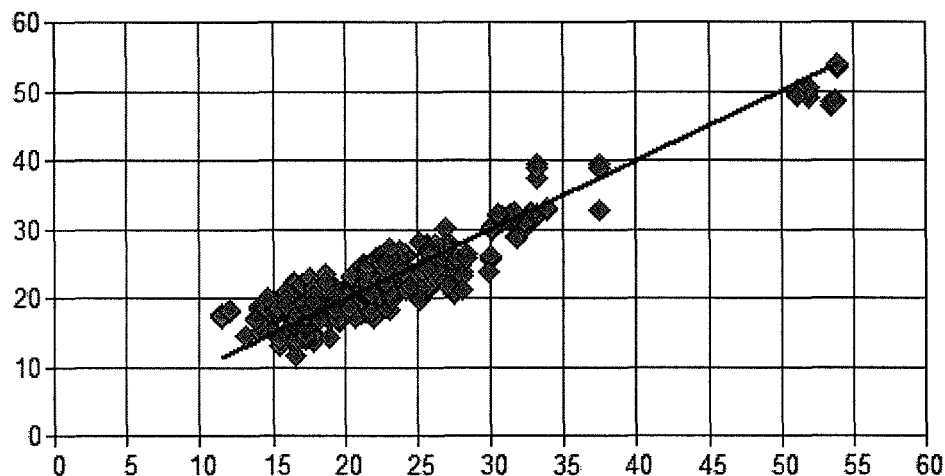
FIG. 3 shows a NIR model for protein in poultry feed processed according to an embodiment of the present application.

A computer-generated cross validation of the NIR protein model for poultry feed is shown in FIG. 3. The model included 29 samples. The $R^2$ for the model was 86.66 and the RMSECV (root mean square error of cross-validation) was 2.68. $R^2$ value indicates how well the data fits the model and how well the observed outcomes are predicted by the model. The RMSECV is a measure of the variation in the data.

Figure 4:
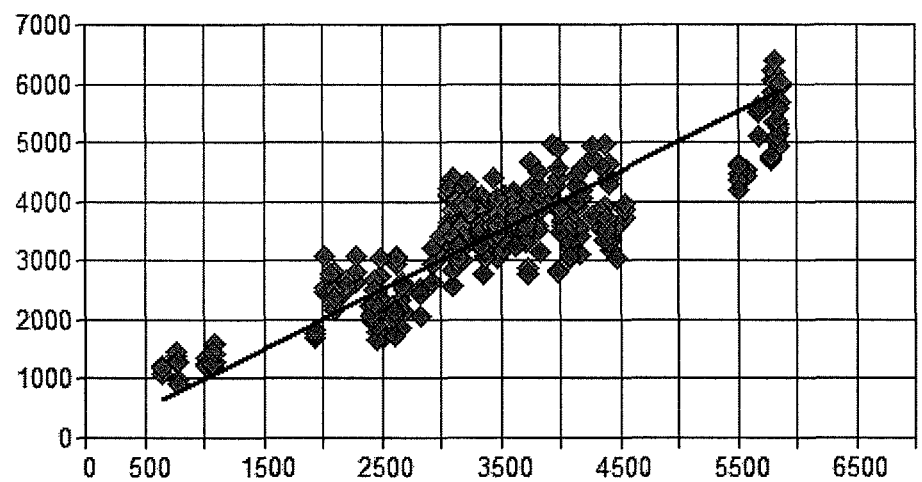
FIG. 4 shows a NIR model for phosphorus in poultry feed processed according to an embodiment of the present application.

A computer-generated cross validation of the NIR phosphorus model for poultry feed is shown in FIG. 4. The model included 24 samples. The $R^2$ for the model was 75.94 and the RMSECV was 554.

Figure 5:
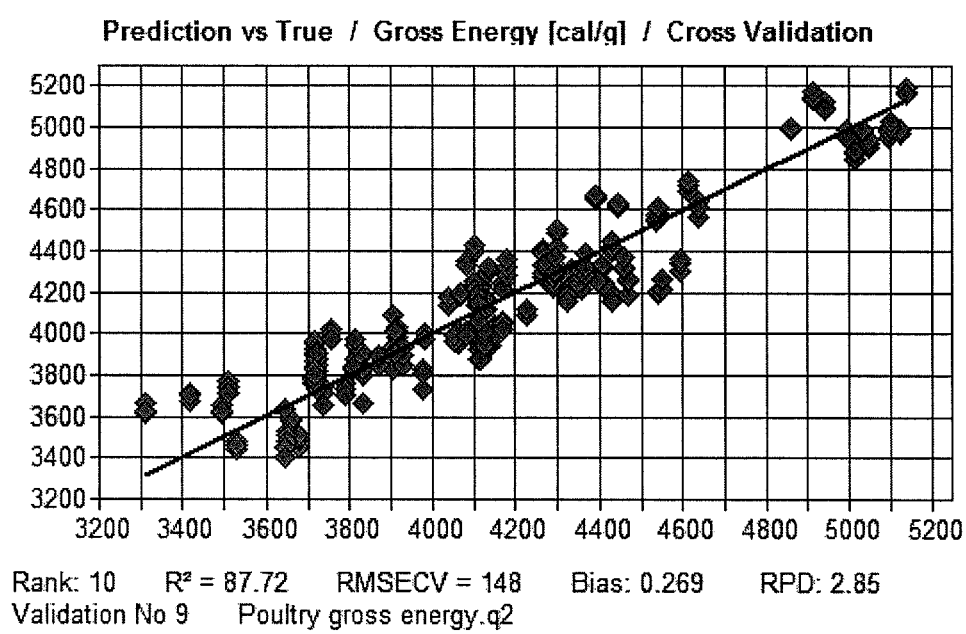
FIG. 5 shows a NIR model for gross energy in poultry feed processed according to an embodiment of the present application.
Figure 6:
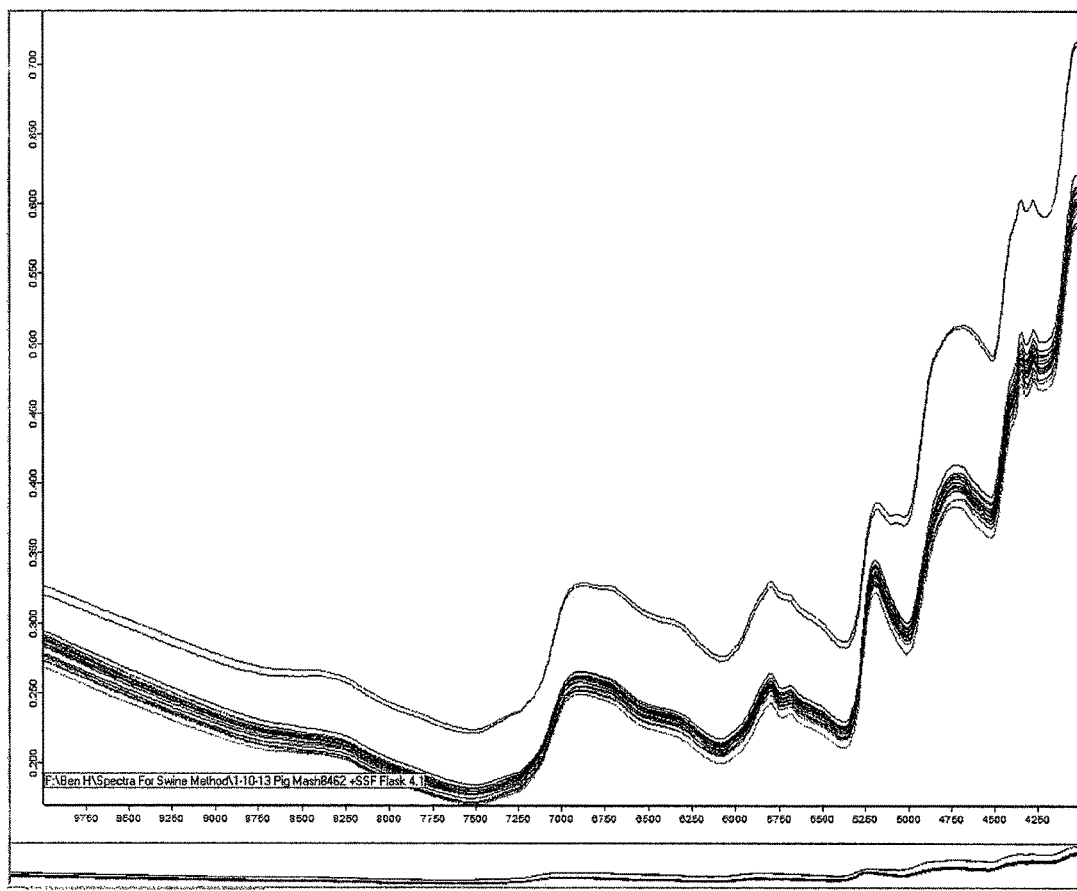
FIG. 6 shows exemplary NIR spectral data for swine feed samples processed according to an embodiment of the present application.

A computer-generated cross validation of the NIR gross energy model for poultry feed is shown in FIG. 5. The model included 18 samples. The $R^2$ for the model was 87.72 and the RMSECV was 148. It is expected that $R^2$ and RMSEV of the models can be improved by increasing the number of samples in the model.
Results—Swine Feed Digestion Assay Swine feed samples were digested according to the digestion assay. The final dry matter portions of digested samples were scanned using the NIR rotating cup assembly to collect NIR reflectance data. An exemplary scan of the digested swine feed samples is shown in FIG. 6.

The digested samples were analyzed by wet chemistry methods for protein and gross energy. The protein content of the digested samples was in the range of 6-47% and gross energy in the range of 3900-5300 cal/g. The protein and gross energy content of each sample was then correlated with the NIR scans to develop NIR models for each component.

Figure 7:
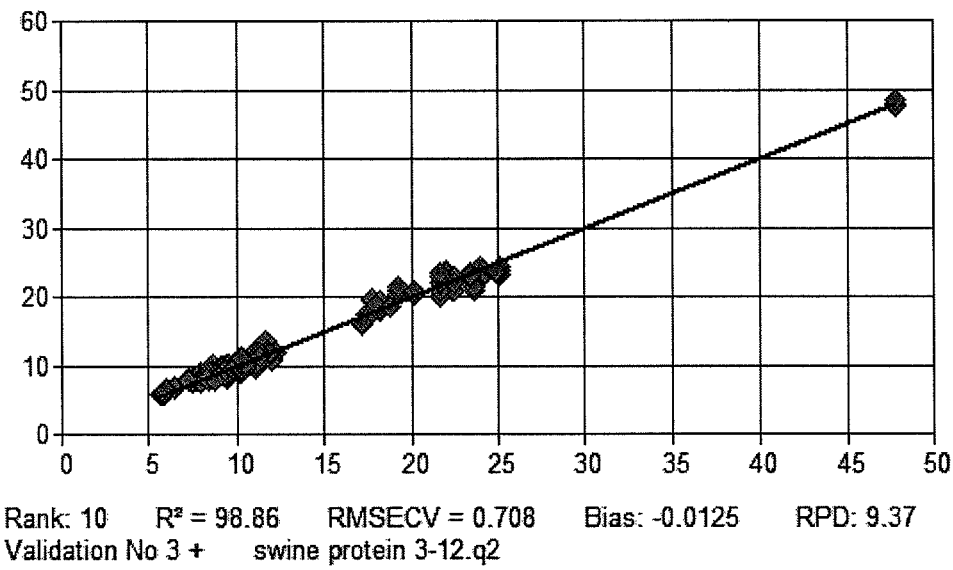
FIG. 7 shows a NIR model for protein in swine feed processed according to an embodiment of the present application.

A computer-generated cross validation of the NIR protein model for swine feed is shown in FIG. 7. The $R^2$ for the model was 98.86 and the RMSECV was 0.708.

Figure 8:
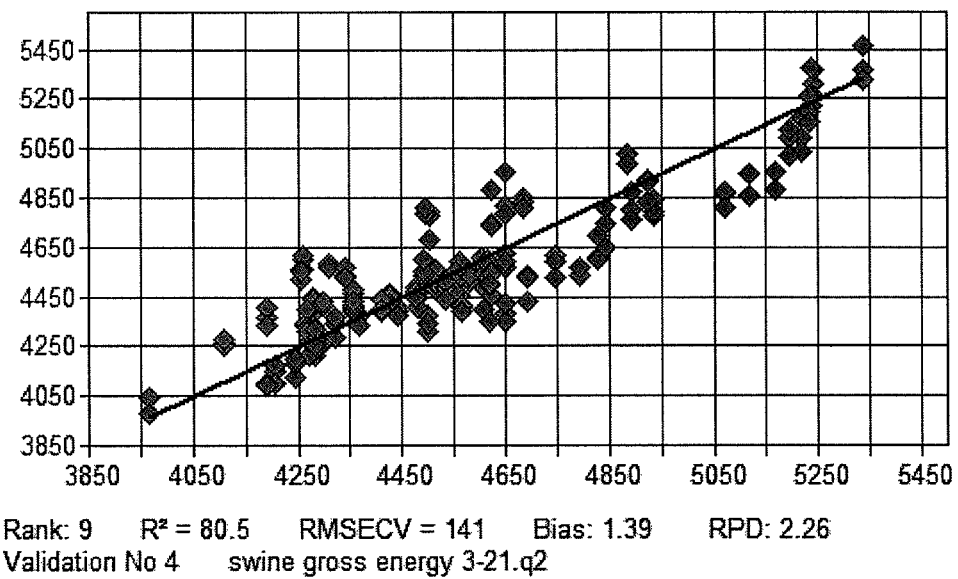
FIG. 8 shows a NIR model for gross energy in swine feed processed according to an embodiment of the present application.

A computer-generated cross validation of the NIR gross energy model for swine feed is shown in FIG. 8. The $R^2$ for the model was 80.5 and the RMSECV was 141.

DISCUSSION

The results show various NIR models that can be developed for use in conjunction with a digestion assay to predicted the content of un-digested (i.e., residual) components in digested feed samples. The protein model for swine feed was particularly successful ($R^2$ of 98.86), even with a relatively low number of samples used in the exemplary model. The model was shown to be highly predictable of actual protein content in digested feed samples and can be used in lieu of performing expensive and time-consuming wet chemistry methods. The accuracy of the models can be increased with an increased number of samples. In particular, it is expected that the predictability of the phosphorus and gross energy models can be improved by including more samples in the models.

Example 2

Validation of the Residual Protein Model for Swine

The predictability of the residual protein model for digest of swine feed was validated. The method of validating is reflective of how the methods described herein are used to analyze a feed sample with unknown characteristics.

A set of samples of swine feed was digested as described in Example 1 and scanned using NIR. Each sample was also characterized for protein content using wet chemistry. The samples were divided into a validation set and model building set. The samples in the model building set were used to create a model as described herein. The validation set was tested in the model to generate a predicted concentration of residual protein for each sample. The predicted concentration for each sample was compared to the concentration of residual protein in the sample as determined using wet chemistry (True). The results are shown in Table 1:

TABLE 1

| File Name | True | Prediction | Difference |
|---|---|---|---|
| Russia Sow Flask 8.2 | 8.84625 | 8.64 | 0.206 |
| Russia Sow Flask 8.1 | 8.84625 | 8.798 | 0.0478 |
| Russia Sow Flask 8.0 | 8.84625 | 8.691 | 0.155 |
| Russia Sow Flask 7.2 | 8.5775 | 8.841 | −0.263 |
| Russia Sow Flask 7.1 | 8.5775 | 8.922 | −0.345 |
| Russia Sow Flask 7.0 | 8.5775 | 8.965 | −0.387 |
| Russia Sow Flask 6.2 | 10.0781 | 9.498 | 0.58 |
| Russia Sow Flask 6.1 | 10.0781 | 9.513 | 0.565 |
| Russia Sow Flask 6.0 | 10.0781 | 9.522 | 0.556 |
| Russia Sow Flask 5.2 | 8.51 | 8.502 | 0.00811 |
| Russia Sow Flask 5.1 | 8.51 | 8.567 | −0.0568 |
| Russia Sow Flask 5.0 | 8.51 | 8.646 | −0.136 |
| Russia Sow Flask 4.2 | 8.44 | 8.314 | 0.126 |
| Russia Sow Flask 4.1 | 8.44 | 8.303 | 0.137 |
| Russia Sow Flask 4.0 | 8.44 | 8.446 | −0.00599 |
| Russia Sow Flask 3.2 | 8.495 | 8.738 | −0.243 |
| Russia Sow Flask 3.1 | 8.495 | 8.871 | −0.376 |

These results show the model had a high degree of predictability of the concentration of residual protein in the samples.

While certain embodiments of the present application of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts disclosed above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method for analyzing feed for swine or poultry comprising steps of:
   (a) digesting in vitro a plurality of samples of animal feed each having an animal feed composition to generate a plurality of digested animal feed samples, wherein each of the plurality of digested animal feed samples comprises at least one residual component, wherein the at least one residual component is selected from the group consisting of protein, phosphorous, fat, gross energy, and carbohydrates, wherein the samples of animal feed consist of swine feed or poultry feed, wherein each animal feed composition comprises one or more of corn, soybean, grain(s), distiller grain(s), legumes, molasses, or a mixture of any thereof, wherein the digesting in vitro comprises at least two phases:
   wherein for swine feed an in vitro digestion phase is conducted for 1 to 6 hours at a pH of less than about 7 and includes use of at least one enzyme comprising pepsin, and wherein another in vitro digestion phase is conducted for 18 hours to 48 hours at neutral pH to an acidic pH of at least 6.0 and includes use of at least one enzyme comprising pancreatin, to generate the plurality of digested animal feed samples,
   wherein for poultry feed, an in vitro digestion phase is conducted that includes use of at least one enzyme comprising phytase, another in vitro digestion phase is conducted at a pH of less than about 7 for 30 minutes to 2 hours and includes use of at least one enzyme comprising pepsin, and an additional in vitro digestion phase is conducted at neutral pH to an acidic pH of at least 6.0 for 30 minutes to 2 hours and includes use of at least one enzyme comprising pancreatin, to generate the plurality of digested animal feed samples;
   (b) separating each of the plurality of digested animal feed samples obtained in step (a) into a solid component and a liquid component;
   (c) scanning the solid component of each of the plurality of digested animal feed samples obtained in step (b) using a near infrared (NIR) spectrophotometer to generate spectral data for each of the plurality of digested animal feed samples;
   (d) determining the concentration of the at least one residual component in each of the plurality of digested animal feed samples using a wet chemistry method;
   (e) generating a computer model comprising a computer implemented method comprising steps of:
      i) receiving spectral data for each of the plurality of digested animal feed samples;
      ii) relating the spectral data for each of the plurality of digested animal feed samples to the concentration of the at least one residual component in a corresponding sample of the plurality of digested animal feed samples; and
      iii) establishing a predictive relationship based on the spectral data and the concentration of the at least one residual component of the plurality of digested animal feed samples to generate the computer model; and
   (f) validating the computer model for analyzing feed for swine or poultry using validation samples, wherein the validation samples comprise a plurality of different samples of the animal feed that are different from the samples used in step (a), comprising comparing a concentration of at least one residual component in each of a plurality of digested samples obtained from the different samples of the animal feed that is predicted from the computer model to a corresponding measured concentration determined by wet chemistry for the at least one residual component in each of the plurality of digested samples obtained from the different samples of the animal feed.

2. The method of claim 1, wherein the step of scanning the solid component of each of the plurality of digested feed samples further comprises the step of mathematically manipulating the spectral data of each of the plurality of digested animal feed samples.

3. The method of claim 1, wherein the wet chemistry method comprises analyzing each sample of the digested feed for the concentration of the at least one residual component selected from the group consisting of protein, phosphorous, fat, gross energy, and carbohydrates.

4. The method of claim 1, wherein each of the samples of animal feed is swine feed.

5. The method of claim 4, wherein the pepsin is porcine pepsin and the pancreatin is porcine pancreatin.

6. The method of claim 4, wherein the animal composition comprises corn.

7. The method of claim 4, wherein the digestion phase and the other digestion phase further include use of an acetate buffer.

8. The method of claim 1, wherein each of the samples of animal feed is poultry feed.

9. The method of claim 8, wherein the animal composition comprises corn.

10. The method of claim 1, wherein the at least one residual component is selected from the group consisting of protein, phosphorous, fat, and gross energy.

11. The method of claim 1, wherein the at least one residual component is selected from the group consisting of protein, fat, and gross energy.

12. The method of claim 1, wherein the validating in step (f) comprises:
   (1) digesting in vitro the plurality of different samples of the animal feed wherein digesting comprises two phases, wherein a phase is conducted at a pH of less than about 7 and includes use of at least one enzyme comprising pepsin, and wherein another phase is conducted at a neutral to acidic pH and includes at least one enzyme comprising pancreatin;
   (2) separating each of the plurality of digested different samples of animal feed obtained in step (1) into a solid component and a liquid component;
   (3) scanning the solid component obtained in step (2) of the plurality of digested different samples of animal feed using a near infrared (NIR) spectrophotometer to generate spectral data for each of the plurality of digested different samples of animal feed;
   (4) predicting the concentration of the at least one residual component in each of the plurality of digested different samples of animal feed using the computer model to obtain predicted concentrations thereof;
   (5) determining the concentration of the at least one residual component in each of the plurality of digested different samples of animal feed using a wet chemistry method to obtain measured concentrations thereof; and
   (6) comparing the predicted concentration of the at least one residual component in each of the plurality of digested different samples of animal feed to a corresponding measured concentration determined by the wet chemistry in making a validation determination on the computer model.

13. The method of claim 12, wherein the separating in step (2) comprises centrifuging or filtering.

14. The method of claim 1, further comprising:
(g) determining a coefficient of determination, $R^2$ value, of the computer model based on comparing a plurality of concentrations predicted for a plurality of validation samples using the computer model with actual concentrations of the validation samples determined by wet chemistry, and
(h) determining if the computer model is validated for analyzing feed for swine or poultry by determining if the $R^2$ value determined in step (g) is at least 50.

15. The method of claim 14, wherein the determining in step (h) if the computer model is validated for analyzing feed for swine or poultry comprises determining if the $R^2$ value determined in step (g) is at least 70.

16. The method of claim 1, wherein the separating in step (b) comprises centrifuging or filtering.

17. The method of claim 16, further comprising freeze-drying the solid component obtained from the separating in step (b) to provide a final dry matter portion thereof prior to step (c), and wherein the solid component scanned in step (c) comprises the final dry matter portion thereof.

18. The method of claim 16, wherein the determining using wet chemistry in step (d) is performed on the solid component of each of the plurality of digested animal feed samples.

* * * * *